(12) United States Patent
McKenna et al.

(10) Patent No.: US 8,428,676 B2
(45) Date of Patent: Apr. 23, 2013

(54) THERMOELECTRIC ENERGY HARVESTING WITH WIRELESS SENSORS

(75) Inventors: Edward McKenna, Boulder, CO (US); Youzhi Li, Longmont, CO (US)

(73) Assignee: Covidien LP, Mansfield, MA (US)

(\*) Notice: Subject to any disclaimer, the term of this patent is extended or adjusted under 35 U.S.C. 154(b) by 430 days.

(21) Appl. No.: 12/751,806

(22) Filed: Mar. 31, 2010

(65) Prior Publication Data

US 2011/0245638 A1   Oct. 6, 2011

(51) Int. Cl.
*A61B 5/1455* (2006.01)

(52) U.S. Cl.
USPC .................................................. 600/323

(58) Field of Classification Search ............. 600/323
See application file for complete search history.

(56) References Cited

U.S. PATENT DOCUMENTS

| | | | |
|---|---|---|---|
| 3,721,813 A | 3/1973 | Condon et al. |
| 4,971,062 A | 11/1990 | Hasebe et al. |
| 4,974,591 A | 12/1990 | Awazu et al. |
| 5,028,787 A | 7/1991 | Rosenthal et al. |
| 5,035,243 A | 7/1991 | Muz |
| 5,065,749 A | 11/1991 | Hasebe et al. |
| 5,084,327 A | 1/1992 | Stengel |
| 5,094,240 A | 3/1992 | Muz |
| 5,275,159 A | 1/1994 | Griebel |
| 5,348,003 A | 9/1994 | Caro |
| 5,429,129 A | 7/1995 | Lovejoy et al. |
| 5,474,065 A | 12/1995 | Meathrel et al. |
| 5,483,646 A | 1/1996 | Uchikoga |
| 5,511,546 A | 4/1996 | Hon |
| 5,619,992 A | 4/1997 | Guthrie et al. |
| 5,666,952 A | 9/1997 | Fuse et al. |
| D393,830 S | 4/1998 | Tobler et al. |
| 5,779,631 A | 7/1998 | Chance |
| 5,871,442 A | 2/1999 | Madarasz et al. |
| 6,006,120 A | 12/1999 | Levin |
| 6,081,742 A | 6/2000 | Amano et al. |
| 6,144,444 A | 11/2000 | Haworth et al. |
| 6,261,236 B1 | 7/2001 | Grimblatov |

(Continued)

FOREIGN PATENT DOCUMENTS

| | | |
|---|---|---|
| DE | 3516338 | 11/1986 |
| DE | 3703458 | 8/1988 |

(Continued)

OTHER PUBLICATIONS

Crilly, et al.; "An Integrated Pulse Oximeter System for Telemedicine Applications," *IEEE Instrumentation and Measurement Technology Conference*, May 19-21, 1997; pp. 102-104; Ottawa, Canada.

(Continued)

*Primary Examiner* — W. B. Perkey
(74) *Attorney, Agent, or Firm* — Fletcher Yoder

(57) ABSTRACT

A system and method for generating power from temperature differences across a thermoelectric energy harvester. The system may include one or more sensing components which, acting alone or in combination, are capable of generating data related to one or more physiological parameters. The system may also include wireless communication circuitry capable of wirelessly transmitting the data related to the one or more physiological parameters. Furthermore, at least one of the one or more sensing components or the wireless communication circuitry may be at least partially powered, directly or indirectly, by energy generated via the thermoelectric energy harvester.

23 Claims, 5 Drawing Sheets

U.S. PATENT DOCUMENTS

| | | | |
|---|---|---|---|
| 6,285,895 B1 | 9/2001 | Ristolainen et al. | |
| 6,353,750 B1 | 3/2002 | Kimura et al. | |
| 6,419,671 B1 | 7/2002 | Lemberg | |
| 6,461,305 B1 | 10/2002 | Schnall | |
| 6,512,937 B2 | 1/2003 | Blank et al. | |
| 6,564,088 B1 | 5/2003 | Soller et al. | |
| 6,589,172 B2 | 7/2003 | Williams et al. | |
| 6,591,122 B2 | 7/2003 | Schmitt | |
| 6,791,689 B1 | 9/2004 | Weckström | |
| 6,793,654 B2 | 9/2004 | Lemberg | |
| 6,916,289 B2 | 7/2005 | Schnall | |
| 6,971,580 B2 | 12/2005 | DeLonzor et al. | |
| 6,992,751 B2 | 1/2006 | Al-Ali | |
| 7,198,778 B2 | 4/2007 | Mannheimer et al. | |
| 7,236,811 B2 | 6/2007 | Schmitt | |
| 7,236,881 B2 | 6/2007 | Schmitt et al. | |
| 7,313,427 B2 | 12/2007 | Benni | |
| 7,469,158 B2 | 12/2008 | Iyer et al. | |
| 7,572,229 B2 | 8/2009 | Yeo et al. | |
| 7,574,244 B2 | 8/2009 | Eghbal et al. | |
| 7,834,263 B2* | 11/2010 | DeSteese et al. | 136/205 |
| 2004/0098009 A1 | 5/2004 | Boecker et al. | |
| 2005/0065414 A1 | 3/2005 | Allen et al. | |
| 2005/0075550 A1 | 4/2005 | Lindekugel | |
| 2005/0113656 A1 | 5/2005 | Chance | |
| 2005/0177034 A1 | 8/2005 | Beaumont | |
| 2005/0197548 A1 | 9/2005 | Dietiker | |
| 2005/0234317 A1* | 10/2005 | Kiani | 600/323 |
| 2005/0280531 A1 | 12/2005 | Fadem et al. | |
| 2006/0058594 A1 | 3/2006 | Ishizuka et al. | |
| 2006/0247501 A1 | 11/2006 | Ali | |
| 2006/0282001 A1 | 12/2006 | Noel et al. | |
| 2007/0049842 A1 | 3/2007 | Hill et al. | |
| 2007/0073121 A1 | 3/2007 | Hoarau et al. | |
| 2007/0100218 A1 | 5/2007 | Sweitzer et al. | |
| 2007/0100219 A1 | 5/2007 | Sweitzer et al. | |
| 2007/0106133 A1 | 5/2007 | Satchwell et al. | |
| 2007/0123756 A1* | 5/2007 | Kitajima et al. | 600/300 |
| 2008/0281168 A1 | 11/2008 | Gibson et al. | |
| 2010/0063368 A1* | 3/2010 | Leuthardt et al. | 600/301 |
| 2010/0179391 A1* | 7/2010 | Quintanar et al. | 600/301 |
| 2011/0213216 A1* | 9/2011 | McKenna et al. | 600/301 |
| 2011/0245637 A1* | 10/2011 | McKenna | 600/310 |
| 2011/0245638 A1* | 10/2011 | McKenna et al. | 600/323 |
| 2012/0203081 A1* | 8/2012 | LeBoeuf et al. | 600/301 |

FOREIGN PATENT DOCUMENTS

| | | |
|---|---|---|
| EP | 0127947 | 12/1984 |
| EP | 0531631 | 3/1993 |
| JP | 5049625 | 3/1993 |
| JP | 6014906 | 1/1994 |
| JP | 6269430 | 9/1994 |
| JP | 7236625 | 9/1995 |
| JP | 2000237170 | 9/2000 |
| JP | 2004159810 | 6/2004 |
| JP | 2004329406 | 11/2004 |
| JP | 2004337605 | 12/2004 |
| JP | 2004351107 | 12/2004 |
| WO | WO8909566 | 10/1989 |
| WO | WO9111137 | 8/1991 |
| WO | WO9947039 | 9/1999 |
| WO | WO2005010568 | 2/2005 |
| WO | WO2005114524 | 12/2005 |
| WO | WO2006109072 | 10/2006 |
| WO | WO2007141121 | 12/2007 |

OTHER PUBLICATIONS

Warren, et al.; "Wearable Sensors and Component-Based Design for Home Health Care," *Proceedings of the Second Joint EMBS/BMES Conference*, Oct. 23-26, 2002; pp. 1871-1872; Houston, Texas.

Lebak, et al.; "Implementation of a Standards-Based Pulse Oximeter on a Wearable, Embedded Platform," *Proceeding of the 25th Annual International Conference of the IEEE EMBS*, Sep. 17-21, 2003; pp. 3196-3198; Cancun, Mexico.

Nagl, et al.; "Wearable Sensor System for Wireless State-of-Health Determination in Cattle," *Proceeding of the 25th Annual International Conference of the IEEE EMBS*, Sep. 17-21, 2003; pp. 3012-3015; Cancun, Mexico.

Pujary, et al.; "Photodetector Size Considerations in the Design of a Noninvasive Reflectance Pulse Oximeter for Telemedicine Applications," *IEEE*, 2003, pp. 148-149.

Wendelken et al.; "The Feasibility of Using a Forehead Reflectance Pulse Oximeter for Automated Remote Triage," *IEEE*, 2004, pp. 180-181.

Watkins et al.; "Low-grade heat energy harvesting using superlattice thermoelectrics for applications in implantable medical devices and sensors", 24th *International Conference on Thermoelectrics*, Jun. 19-23, 2005, IEEE.

Park; "Overview of Energy Harvesting Systems (for low-power electronics)"; The First Engineering Institute Workshop; Energy Harvesting; Jun. 28, 2005; slides 1-30; Los Alamos National Laboratory.

* cited by examiner

US 8,428,676 B2

THERMOELECTRIC ENERGY HARVESTING WITH WIRELESS SENSORS

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Wireless sensors have been developed for use in measuring physiological parameters of a patient. Powering of these devices may present a challenge as there are no wires connected to the sensor available to provide power to the sensors. While internal power sources such as batteries may be utilized, problems may exist in which the internal power source is drained. Accordingly, alternate powering methods may be useful.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to a system and method for harnessing temperature differences into power for powering electronic devices. The system may include one or more thermoelectric sensitive structures that when differences in temperature are encountered, harvested charging signals are generated based on the converting the temperature differences into electromagnetic charging signals. The system may include one or more elements that may receive the generated electromagnetic charging signals and may utilize the electromagnetic charging signals to charge a power source, such as a rechargeable battery, of a device. Additionally and/or alternatively, the electromagnetic charging signals may be utilized to power the device directly. The device may include, but is not limited to, pulse oximetry sensors, pulse oximetry monitors, portable pulse oximeters, and/or medical implants. That is, the system may include a device with one or more sensing components which, acting alone or in combination, are capable of generating data related to one or more physiological parameters. The system may also include wireless communication circuitry capable of wirelessly transmitting the data related to the one or more physiological parameters. In one embodiment, at least one of the one or more sensing components or the wireless communication circuitry of the device may be at least partially powered, directly or indirectly, by energy harvested from differences in temperatures between two surfaces of a thermoelectric energy harvester.

Figure 1:
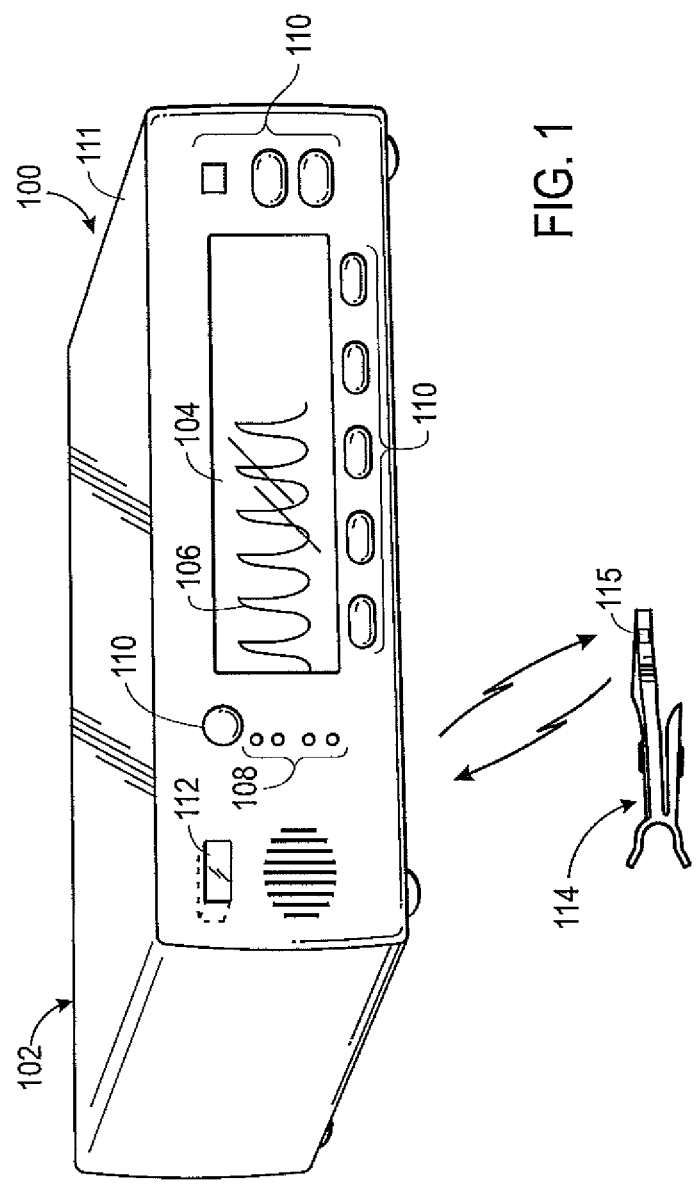
FIG. 1 illustrates a perspective view of a wireless power system including an electronic device, such as a pulse oximeter, in accordance with an embodiment.

Turning to FIG. 1, a perspective view of a medical device is illustrated in accordance with an embodiment. The medical device may be a pulse oximeter 100. The pulse oximeter 100 may include a monitor 102, such as those available from Nellcor Puritan Bennett LLC. The monitor 102 may be configured to display calculated parameters on a display 104. As illustrated in FIG. 1, the display 104 may be integrated into the monitor 102. However, the monitor 102 may be configured to provide data via a port to a display (not shown) that is not integrated with the monitor 102. The display 104 may be configured to display computed physiological data including, for example, an oxygen saturation percentage, a pulse rate, and/or a plethysmographic waveform 106. As is known in the art, the oxygen saturation percentage may be a functional arterial hemoglobin oxygen saturation measurement in units of percentage $SpO_2$, while the pulse rate may indicate a patient's pulse rate in beats per minute. The monitor 102 may also display information related to alarms, monitor settings, and/or signal quality via indicator lights 108.

To facilitate user input, the monitor 102 may include a plurality of control inputs 110. The control inputs 110 may include fixed function keys, programmable function keys, and soft keys. Specifically, the control inputs 110 may correspond to soft key icons in the display 104. Pressing control inputs 110 associated with, or adjacent to, an icon in the display may select a corresponding option. The monitor 102 may also include a casing 111. The casing 111 may aid in the protection of the internal elements of the monitor 102 from damage.

The monitor 102 may further include a transceiver 112. The transceiver 112 may allow for wireless operation signals to be transmitted to and received from an external sensor 114. In this manner, the monitor 102 and the sensor 114 may communicate wirelessly. The sensor 114 may be of a disposable or a non-disposable type. Furthermore, the sensor 114 may obtain readings from a patient that can be used by the monitor 102 to calculate certain physiological characteristics such as the blood-oxygen saturation of hemoglobin in arterial blood, the volume of individual blood pulsations supplying the tissue, and/or the rate of blood pulsations corresponding to each heartbeat of a patient. As will be discussed in greater detail below, the sensor 114 may include a charging device 115, respectively, for harnessing of energy for use by the sensor 114.

Figure 2:
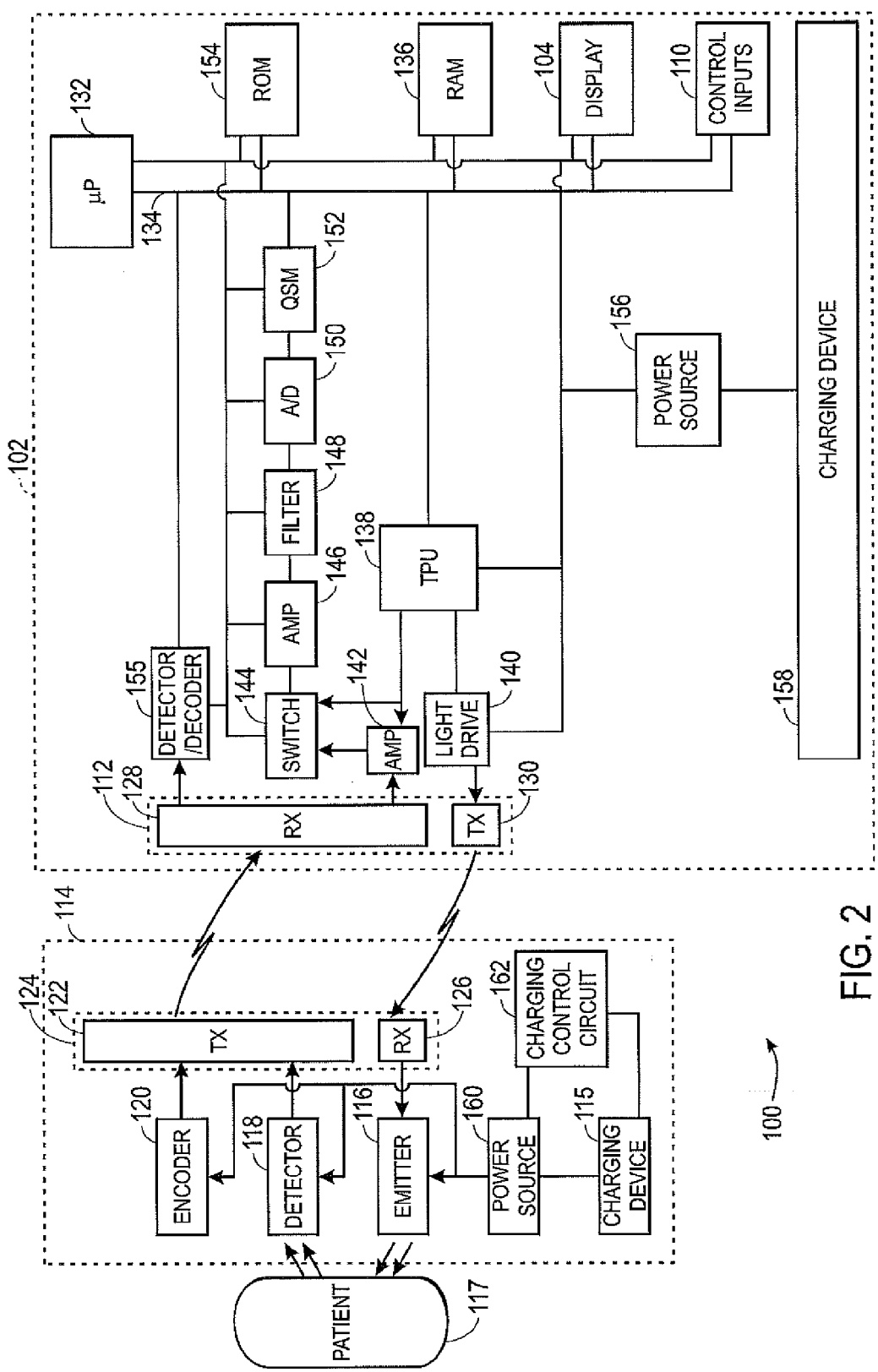
FIG. 2 illustrates a simplified block diagram of the pulse oximeter in FIG. 1, according to an embodiment.

Turning to FIG. 2, a simplified block diagram of the pulse oximeter 100 is illustrated in accordance with an embodiment. Specifically, certain components of the sensor 114 and the monitor 102 are illustrated in FIG. 2, As previously noted, the sensor 114 may include a charging device 115. The sensor 114 may also include an emitter 116, a detector 118, and an encoder 120. It should be noted that the emitter 116 may be capable of emitting at least two wavelengths of light, e.g., RED and infrared (IR) light, into the tissue of a patient 117 to calculate the patient's 117 physiological characteristics, where the RED wavelength may be between about 600 nanometers (nm) and about 700 nm, and the IR wavelength may be between about 800 nm and about 1000 nm. Alternative light sources may be used in other embodiments. For example, a single wide-spectrum light source may be used, and the detector 118 may be capable of detecting certain wavelengths of light. In another example, the detector 118 may detect a wide spectrum of wavelengths of light, and the monitor 102 may process only those wavelengths which are of interest for use in measuring, for example, water fractions, hematocrit, or other physiologic parameters of the patient 117. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

Additionally the sensor 114 may include an encoder 120, which may contain information about the sensor 114, such as what type of sensor it is (e.g., whether the sensor is intended for placement on a forehead or digit) and the wavelengths of light emitted by the emitter 116. This information may allow the monitor 102 to select appropriate algorithms and/or calibration coefficients for calculating the patient's 117 physiological characteristics. Additionally, the encoder 120 may include information relating to the proper charging of the sensor 112. The encoder 120 may, for instance, be a memory on which one or more of the following information may be stored for communication to the monitor 102; the type of the sensor 114; the wavelengths of light emitted by the emitter 116; the proper calibration coefficients and/or algorithms to be used for calculating the patient's 117 physiological characteristics; and/or information regarding a charging device for the sensor 114. The sensor 114 may be any suitable physiological sensor, such as those available from Nellcor Puritan Bennett LLC.

Signals from the detector 118 and the encoder 120 (if utilized) may be transmitted to the monitor 102 via a transmitter 122 that may be located in a transceiver 124. The transceiver 124 may also include a receiver 126 that may be used to receive signals form the monitor 102. As may be seen, the receiver 126 may transmit received signals to the emitter 116 for transmission to a patient 117. The transmitter 122 may receive signals from both the detector 118 and the encoder 120 for transmission to the monitor 102. As previously described, the signals used in conjunction with the emitter 116 and the detector 118 may be utilized for the monitoring of physiologic parameters of the patient 117 while the signals from the encoder may contain information about the sensor 114 to allow the monitor 102 to select appropriate algorithms and/or calibration coefficients for calculating the patient's 117 physiological characteristics.

As previously discussed, the monitor 102 may include a transceiver 112. The transceiver 112 may include a receiver 128 and a transmitter 130. The receiver 128 may receive transmitted signals from the transmitter 122 of the sensor 114 while the transmitter 130 of the monitor 102 may operate to transmit signals to the receiver 126 of the sensor 114. In this manner, the sensor 114 may wirelessly communicate with the monitor 102 (i.e., the sensor 114 may be a wireless sensor 114). The monitor 102 may further include one or more processors 132 coupled to an internal bus 134. Also connected to the bus may be a RAM memory 136 and the display 104. A time processing unit (TPU) 138 may provide timing control signals to light drive circuitry 140, which controls (e.g., via the transmitter 130), when the emitter 116 is activated, and if multiple light sources are used, the multiplexed timing for the different light sources. TPU 138 may also control the gating-in of signals from detector 118 through an amplifier 142 and a switching circuit 134. The amplifier 142 may amplify, for example, the signals from the detector 118 received at the receiver 128. The TPU 138 may control the gating-in of signals from detector 118 through an amplifier 142 to insure that the signals are sampled at the proper time, which may depend at least in part upon which of multiple light sources is activated, if multiple light sources are used. The received signal from the detector 118 may be passed through an (optional) amplifier 146, a low pass filter 148, and an analog-to-digital converter 150 for amplifying, filtering, and digitizing the electrical signals the from the sensor 114. The digital data may then be stored in a queued serial module (QSM) 152, for later downloading to RAM 136 as QSM 152 fills up. In an embodiment, there may be multiple parallel paths of separate amplifier, filter, and A/D converters for multiple light wavelengths or spectra received.

In an embodiment, based at least in part upon the received signals corresponding to the light received by detector 118, processor 122 may calculate the oxygen saturation using various algorithms. These algorithms may use coefficients, which may be empirically determined, and may correspond to the wavelengths of light used. The algorithms may be stored in a ROM 154 and accessed and operated according to processor 122 instructions. The monitor 102 may also include a detector/decoder 155 that may receive signals (via the receiver 128) from the encoder 120. The detector/decoder 155 may, for instance, decode the signals from the encoder 120 and may provide the decoded information to the processor 132. The decoded signals may provide information to the processor such as the type of the sensor 114 and the wavelengths of light emitted by the emitter 116 so that proper calibration coefficients and/or algorithms to be used for calculating the patient's 117 physiological characteristics may be selected and utilized by the processor 132.

The monitor 102 may also include a power source 156 that may be used to transmit power to the components located in the monitor 102. In one embodiment, the power source 156 may be one or more batteries, such as a rechargeable battery. The battery may be user-removable or may be secured within the housing of the monitor 102. Use of a battery may, for example, allow the oximeter 100 to be highly portable, thus allowing a user to carry and use the oximeter 100 in a variety of situations and locations. Additionally, the power source 156 may include AC power, such as provided by an electrical outlet, and the power source 156 may be connected to the AC power via a power adapter through a power cord (not shown). This power adapter may also be used to directly recharge one or more batteries of the power source 156 and/or to power the pulse oximeter 100. In this manner, the power adapter may operate as a charging device 158.

The sensor 114 may also include a charging control circuit 162, which may, for example, allow for the adaptive control of energy harvested from the charging device 115 for use in the power source 160 of the sensor 114. In one embodiment, the power source 160 may be one or more batteries, such as a rechargeable battery that may be user-removable or may be secured within the housing of the sensor 114. Alternatively, the power source 160 may be one or more capacitors for storage of charge. The charging control circuit 162 may, for example, include a processing circuit that may determine the current level of charge remaining in the power source 160, as well as the current amount of power being harvested by the charging device. For example, the charging control circuit 162 may determine if the charging device 115 is generating too little power to charge the power source 160. In response to determining that the charging device 115 is generating too little power to charge the power source 160 and that the power source 160 is low on power, the charging control circuit 162 may generate an error signal that may be transmitted to the monitor 102 for generation of a corresponding error message for display on the display 104 of the monitor 102 by, for example, the processor 132. The error message may indicate to a user that the sensor 102 is low on power and may also direct the user to take action, such as changing the power source 160 (i.e., installing new batteries), charging the power source 160 (i.e. by plugging the sensor 102 into a charging unit or into an electrical outlet via a power adapter). Alternatively, the error message may indicate to a user that the recharging system of the sensor is potentially malfunctioning, and may direct the user, for example, to use replace the sensor 114. In one embodiment, the error message may be generated when the charging control circuit 162 determines that the power source 160 has reached a certain charge level, for example 20% of the total charge remains in the power source 160.

Figure 3:
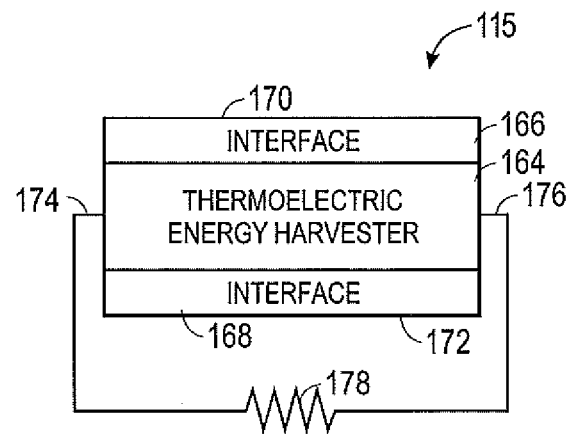
FIG. 3 illustrates the charging device of FIG. 1, in accordance with an embodiment.

The charging device 115 may be one of a multitude of energy harvesting components that utilize, for example, thermoelectric power generation techniques. Through use of these techniques, power may be harvested, for example, through differences in temperatures across the charging device 115, which may be converted to electricity for directly recharging one or more batteries (or capacitors) of the power source 160 and/or to power the sensor 114. FIG. 3 illustrates a first embodiment of the charging device 115.

The charging device 115 may include a thermoelectric energy harvester 164. The charging device 115, as well as the energy harvesters 164, may be, for example, microelectromechanical systems (MEMS) and/or nanoelectromechanical systems (NEMS) made up of components sized between approximately 100 nanometers and 100 micrometers. However, the energy harvester 164, as well as the components that make up the energy harvester 164, may also be larger than MEMS and NEMS described above.

Surrounding the thermoelectric energy harvester 164 may be one or more interface layers 166 and 168. The interface layers 166 and 168 may be, for example, outer layers of the sensor 114, such as bandages. Accordingly, the thermoelectric energy harvester 164 may be embedded between the outer portions of the sensor 114. For example, upper portion 170 of interface layer 166 may contact the skin of a patient 117 when in use, while lower portion 172 of interface layer 168 may contact air surrounding the sensor 117 the skin of a patient 117 when in use. Furthermore, while two interface layers 166 and 168 are illustrated, in one embodiment, interface layer 166 may be removed such that the thermoelectric energy harvester 164 may contact the skin of a patient 117 directly. Additionally and/or alternatively, interface layer 168 may be removed such that the thermoelectric energy harvester 164 may directly contact the air surrounding the sensor 114. Thus, interface layers 166 and 168 may be removed to, for example, allow for direct contact to thermal conditions.

Leads 174 and 176 may be connected to the thermoelectric energy harvester 164. The leads 174 and 176 may also be connected to a load 178. When the thermoelectric energy harvester 164 is exposed to a difference in temperature, such as the difference between the temperature of the skin of a patient 117 and the temperature of ambient air surrounding a patient 117, the temperature differential across the thermoelectric energy harvester 164 may produce a voltage and a current across the load 178 (as transmitted via leads 174 and 176). Accordingly, when, for example, the load 178 is substituted for the power source 160, the power generated via the thermal differential may be harvested and supplied to the power source 160 as an electromagnetic charging signal. An example of a thermoelectric energy harvester 164 of the charging device 115 is illustrated in FIG. 4.

Figure 4:
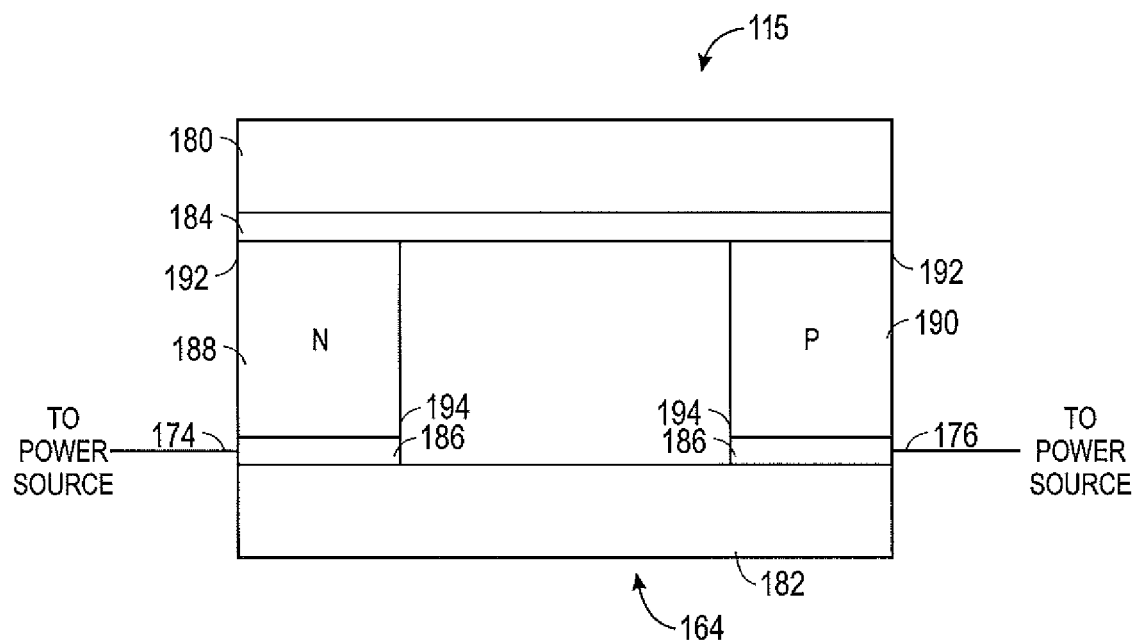
FIG. 4 illustrates a thermoelectric energy harvester of the charging device of FIG. 1, in accordance with an embodiment.

The thermoelectric energy harvester 164 illustrated in FIG. 4 may include one or more substrate layers 180 and 182, conductive layers 184 and 186, and one or more thermoelectric materials 188 and 190. Also included are leads 174 and 176 coupled to the thermoelectric energy harvester 164. Substrate layers 180 and 182 may include a ceramic, Aluminum Nitride (AlN), Alumina ($Al_2O_3$), $SiO_2$, or any other electrically insulating and thermally conducting material. The substrate layers 180 and 182 may be, for example, approximately between 100 and 2000 micrometers (μm) in thickness. Coupled to each of the substrate layers 180 and 182 is a conductive layer 184 and 186, respectively. These conductive layers 184 and 186 may include gold, aluminum, copper, or any other electrically conductive material. The conductive layers 184 and 186 may be, for example, approximately between 25 and 500 μm in thickness. As illustrated, leads 174 and 176 may be attached to one of the conductive layers, for example, layer 186. Additionally coupled to each of the conductive layers 184 and 186 are thermoelectric materials 188 and 190. As illustrated, the thermoelectric materials 188 and 190 are electrically coupled in series and thermally coupled in parallel. The thermoelectric materials 188 and 190 may be, for example, approximately between 1000 and 10,000 μm in thickness and may also be semiconductors.

For example, thermoelectric material 188 may include Bismuth telluride ($Bi_2Te_3$), Lead telluride (PbTe), cobalt triantimonide ($CoSb_3$), Silicon-germanium (SiGe), or $La_3Te_4$. The thermoelectric material 188 may also be doped by introducing impurities into the thermoelectric material 188 to change its electrical properties, in this case, to introduce an impurity with a surplus of electrons to generate an N-type thermoelectric material. Thermoelectric material 190 may include $SbTe_3$, PbTe, SiGe, $CeFe_4Sb_{12}$, or $Yb_{14}MnSb_{11}$. The thermoelectric material 190 may also be doped by introducing an impurity with a surplus of free charge carriers (holes) to generate a P-type thermoelectric material.

As illustrated, the thermoelectric energy harvester 164 may generate electricity in the presence of a temperature differences between substrate layers 180 and 182. For example, substrate layer 180 may be coupled to interface layer 166 while substrate layer 182 may be coupled to interface layer 168. Furthermore, a heat source, such as the skin of a patient 117, may be adjacent to substrate layer 180, while a heat sink, such as the ambient air surrounding a patient 117, may be adjacent to substrate layer 182. Accordingly, because substrate layers 180 and 182 are thermally conductive, a temperature difference may be experienced at the upper portion 192 and the lower portion 194 of the thermoelectric materials 188 and 190.

In thermoelectric material 188, free electrons may carry both charge and heat. Similarly, in thermoelectric material 190, holes may carry both charge and heat. Thus, when the portions 192 and 194 of thermoelectric materials 188 and 190 are exposed to different temperatures, free electrons in thermoelectric material 188 may flow from the heated portion 192 of thermoelectric material 188 to the cooler portion 194 of thermoelectric material 188. This may generate a positive charge at the upper portion 192 and a negative charge at the lower portion 194 of thermoelectric material 188. Simultaneously, holes in thermoelectric material 190 may flow from the heated portion 192 of thermoelectric material 190 to the cooler portion 194 of thermoelectric material 190, creating a positive charge at the upper portion 192 and a negative charge at the lower portion 194 of thermoelectric material 190. Furthermore, by connecting conductive layer 184 between the upper portion 192 of the thermoelectric materials 188 and 190, and by connecting leads 174 and 176 to the lower portion 194 of the thermoelectric materials 188 and 190 (as well as to the power source 160), a circuit may be completed (closed). Closure of this circuit may allow for the flow of current through the thermoelectric energy harvester 164 to the power source 160 for charging of the power source 160 and/or powering of the sensor 114.

It may further be advantageous to increase the amount of power generated by the charging device 115 by including more than one thermoelectric energy harvester 164. Accordingly, FIG. 5 illustrates two thermoelectric energy harvesters 164 connected in series.

Figure 5:
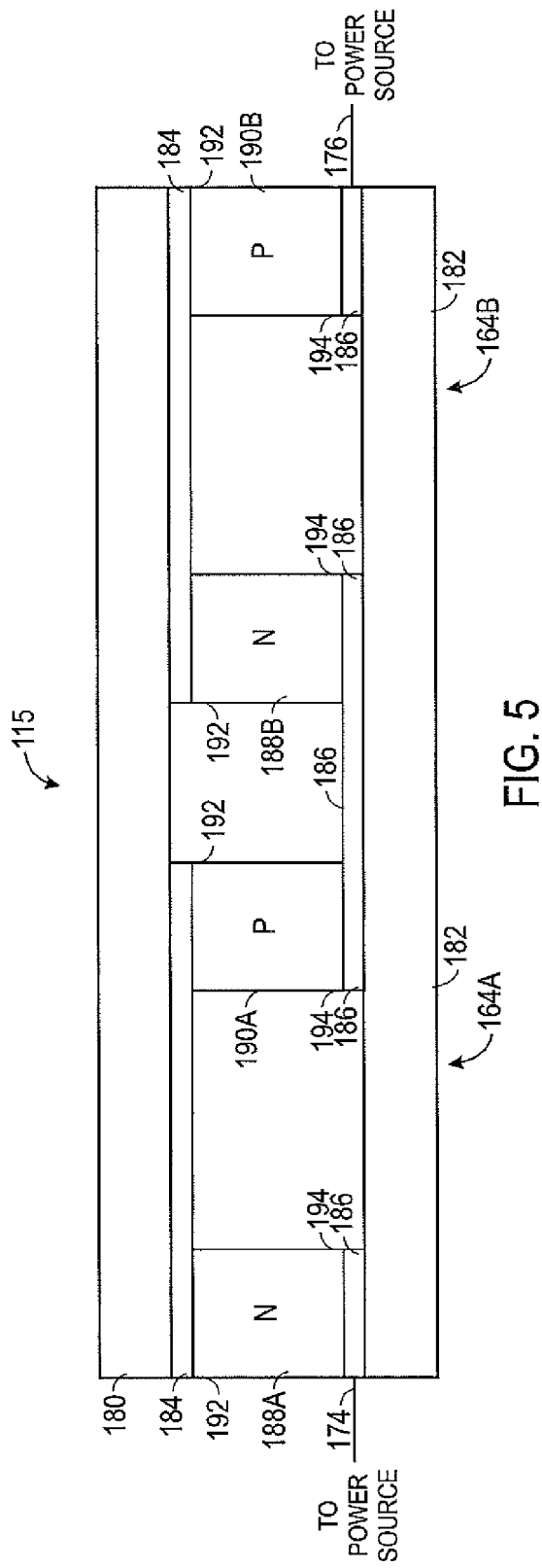
FIG. 5 illustrates a plurality of thermoelectric energy harvesters of the charging device of FIG. 1, in accordance with an embodiment.

The charging device 115 illustrated in FIG. 5 includes a first thermoelectric energy harvester 164a and a second thermoelectric energy harvester 164b. The thermoelectric energy harvesters 164a and 164b may be identical in makeup and operation to thermoelectric energy harvester 164 described above. For example, thermoelectric energy harvester 164a includes thermoelectric material 188a and thermoelectric material 190a, while thermoelectric energy harvester 164b includes thermoelectric material 188b and thermoelectric material 190b. Furthermore, these thermoelectric energy harvesters 164a and 164b are thermally connected in parallel and electrically coupled in series, as described below.

To complete an electrical circuit between the thermoelectric energy harvesters 164a and 164b and the power source 160, lead 174 may be coupled to the conductive layer 186 adjacent to thermoelectric material 188a. Additionally, conductive layer 184 may be coupled to the upper portion 192 of the thermoelectric materials 188a and 190a. Conductive layer 186 may also be coupled to the lower portion 194 of the thermoelectric materials 190a and 188b, while upper portion 192 of thermoelectric materials 188b and 190b may be coupled via conductive layer 184. Finally, the lower portion 194 of thermoelectric material 190b may be connected to lead 176. By coupling the thermoelectric energy harvesters 164a and 164b in this manner (in series), current may flow through the thermoelectric energy harvesters 164a and 164b for charging of the power source 160 and/or current may flow through the thermoelectric energy harvesters 164a and 164b to the sensor 114 for direct powering when the upper and lower portions 192 and 194 of the thermoelectric energy harvesters 164a and 164b are exposed to temperature differences.

Figure 6:
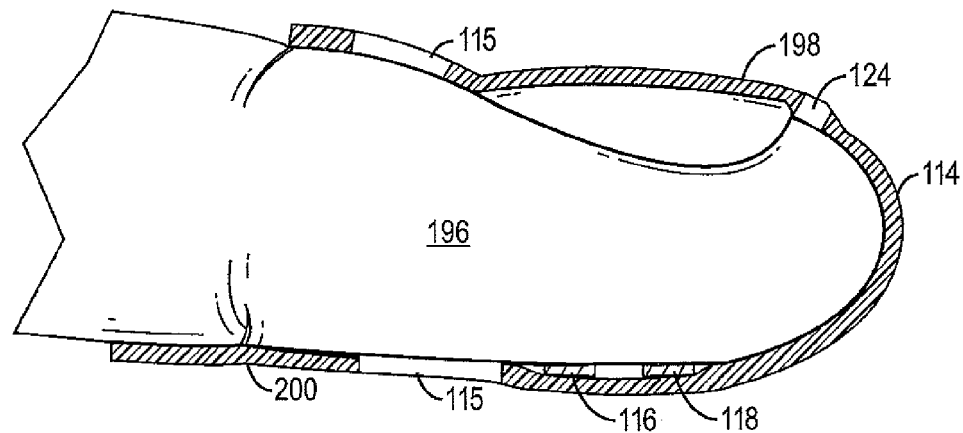
FIG. 6 illustrates a first placement of the charging device and sensor of FIG. 1, in accordance with an embodiment.

The location of one or more charging devices 115 may impact the area available for placement of multiple thermoelectric energy harvesters 164. FIG. 6 illustrates various placement locations of one or more charging devices 115 in conjunction with a sensor 114. The sensor 114 may be utilized in conjunction with a finger 196 of a patient 117. As may be seen, the emitter 116 and the detector 118, as well as the transceiver 124 are illustrated as elements of the sensor 114. As depicted, the emitter 116 and detector 118 may be arranged in a reflectance-type configuration in which the emitter 116 and detector 118 are typically placed on the same side of the sensor site. Reflectance type sensors may operate by emitting light into the tissue (e.g., finger 196) and detecting the reflected light that is transmitted and scattered by the tissue. That is, reflectance type sensors detect light photons that are scattered back to the detector 118. The sensor 114 may alternatively be configured as a transmittance type sensor whereby the emitter 116 and detector 118 are typically placed on differing sides of the sensor site. In this manner, the detector 118 may detect light that has passed through one side of a tissue site to an opposite side of the tissue site.

As illustrated in both FIG. 6, the sensor 114 may also include one or more charging stations 115. The charging stations 115 may include one or more thermoelectric energy harvesters 164, detailed above. In one embodiment, a charging station 115 may be located on a top side 198 of the sensor 114. Additionally and/or alternatively, a charging station 115 may be located on the bottom side 200 of the sensor 114. Each of these charging stations 115 may be integrated into the sensor 114, or affixed thereto. Furthermore, these charging stations 115 may operate independently, or may be electrically coupled to one another to increase the overall airflow that may be harvested for use by the sensor 114. Additionally, one or more charging stations 115 external to the sensor 114 may be utilized.

Figure 7:
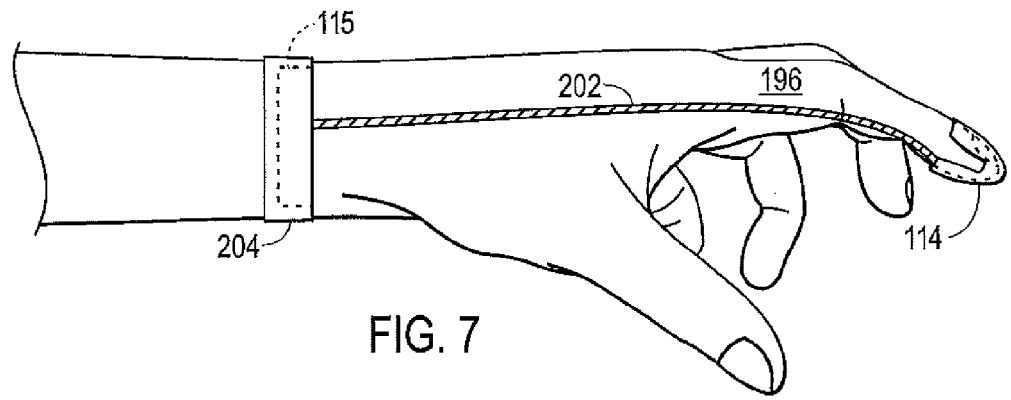
FIG. 7 illustrates a second placement of the charging device and sensor of FIG. 1, in accordance with an embodiment.

FIG. 7 illustrates an embodiment whereby the charging device 115 is located externally from the sensor 114. As illustrated, the charging device 115 may be attached to the sensor 114 via a lead 202. The lead 202 may be an electrical conductor, such as a power cable, that transmits harvested power to the sensor 114. As such, the lead 202 may include leads 174 and 176. The lead 202 may terminate with the charging device 115 which may be integrated into (or be attached to) a bracelet 204. The bracelet 204 may be, for example, a medical bracelet. Furthermore, the lead 202 may be connected to and separated from the charging device 115. That is, the lead 202 may be separable (i.e., releasable) from the charging device 115, the bracelet 204, and/or the sensor 114. Alternatively, the lead 202 may be permanently affixed to the charging device 115 and/or the bracelet 204. Regardless, by separating the charging device 115 from the sensor 114, more available area in the bracelet 204 may be available for harvesting of energy via, for example, patient 117 generated heat. That is, with greater area available for the charging device 115, a greater number of thermoelectric energy harvesters 164 may be utilized, thus increasing the overall amount of energy that may be harvested.

Figure 8:
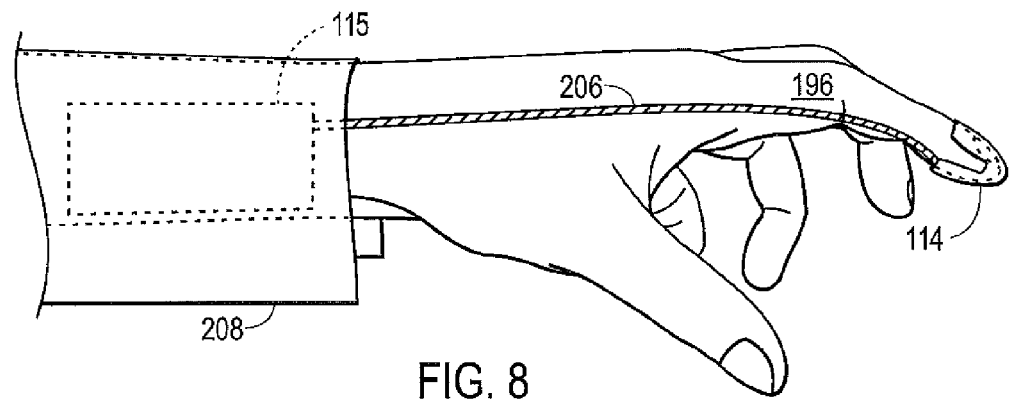
FIG. 8 illustrates a third placement of the charging device and sensor of FIG. 1, in accordance with an embodiment.

FIG. 8 illustrates a second embodiment whereby the charging device 115 may be located externally from the sensor 114. As illustrated, the charging device 115 may be attached to the sensor 114 via lead 206. The lead 206 may be an electrical conductor, such as a power cable, that transmits power to the sensor 114 and may terminate with the charging device 115 which may be integrated into (or be attached to) a garment 208. Again, the lead 206 may be separable (i.e., releasable) from the charging device 115, the garment 208, and/or the sensor 114, and may include leads 174 and 176.

The garment 208 may be, for example, a shirt or a sleeve of a shirt. The use of the a garment 208 to house the charging device 115 may allow for the charging device 115 to be expanded in size, or for more than one charging devices 115 to be utilized in conjunction, while still allowing for the garment 208 to be comfortably worn. Thus a greater number of thermoelectric energy harvesters 164 may be utilized, which may increase the overall amount of energy that may be harvested. Additionally, by utilizing a large area, such as the garment 208, a plurality of regions of the patient 117 may be utilized to harvest energy from. That is, the chest, arms, etc. of the patient 117 may be translated into surface area for the placement thermoelectric energy harvesters 164 for use by the sensor 114.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims.

What is claimed is:

1. A physiological sensor, comprising:
    a generating structure configured to generate power in response to differences in temperature, wherein a first portion of the generating structure is configured to directly contact a patient's tissue and a second portion of the generating structure is configured to directly contact surrounding air;
    a sensing component configured to generate data related to one or more physiological parameters; and
    wireless communication circuitry configured to wirelessly transmit the data related to the one or more physiological parameters, wherein the sensing component or the wireless communication circuitry are at least partially powered, directly or indirectly, by the power generating structure.

2. The physiological sensor of claim 1, comprising an energy storing structure that is at least partially charged by the power generating structure, wherein the sensing component is at least partially powered by the energy storing structure.

3. The physiological sensor of claim 2 wherein the energy storing structure comprises a chargeable battery or a capacitor.

4. The physiological sensor of claim 1, wherein the power generating structure comprise a thermoelectric energy harvester.

5. A power module for a physiological sensor, comprising:
    a power generating structure configured to generate power in response to differences in temperature, wherein a first portion of the generating structure is configured to directly contact a patient's tissue and a second portion of the generating structure is configured to directly contact surrounding air; and
    a connector capable of releasably connecting to a physiological sensor, wherein the connector is capable of transmitting power generated by the power generating structures to the physiological sensor when connected.

6. The power module of claim 5, comprising an energy storing structure that is at least partially charged by the power generating structure.

7. The power module of claim 5, wherein the power module comprises a bracelet coupled to at least one of the power generating structure or the connector.

8. The power module of claim 7, wherein the power generating structure is affixed to the bracelet.

9. The power module of claim 5, wherein the power module comprises a garment coupled to at least one of the power generating structure or the connector.

10. The power module of claim 9, wherein the power generating structure is integrated into the garment.

11. A method for powering a wireless sensor, comprising the acts of:
    generating power using a power generating structure in response to differences in temperature, wherein a first portion of the power generating structure is positioned directly on a patient's tissue and a second portion of the power generating structure is in direct contact with surrounding air; and
    providing the power to the sensor, wherein the sensor comprises a sensor housing positioned on a patient, the sensor housing comprising a light generating component and a light detecting component.

12. The method of claim 11, wherein the power is stored in a battery or capacitor prior to being provided to the sensor.

13. The method of claim 11, wherein the power is generated at a location separate from the sensor housing.

14. The method of claim 13, wherein the location separate from the sensor housing is at a bracelet or a garment worn by the patient.

15. The method of claim 11, comprising utilizing the power by the sensor to generate data related to one or more physiological parameters of the patient.

16. A monitoring system, comprising:
a wireless sensor, comprising:
   a light generating component;
   a light detecting component configured to detect light generated by the light generating component;
   a wireless transmitter configured to wirelessly transmit a signal based on the light detected by the light detecting component; and
   a power generating component that generates power in response to differences in temperature, wherein a first portion of the generating structure is configured to directly contact a patient's tissue and a second portion of the generating structure is configured to directly contact surrounding air, and wherein the generated power is provided to one or more of the light generating component, the light detecting component, or the wireless transmitter; and
a monitor capable of receiving the signal.

17. The monitoring system of claim 16, wherein the light generating component, light detecting component, and the power generating component are incorporated into a housing of the wireless sensor.

18. The monitoring system of claim 16, wherein the light generating component and light detecting component are positioned within a sensor housing, and the power generating component is separate from, but in communication with, the sensor housing.

19. The monitoring system of claim 16, comprising an energy storage component capable of storing the generated power prior to the power being provided to one or more of the light generating component, the light detecting component, or the wireless transmitter.

20. The monitoring system of claim 16, wherein the power generating component comprises a thermoelectric energy harvester.

21. The physiological sensor of claim 1, wherein the sensing component and the power generating component are incorporated into a sensor housing, and the sensor housing is configured to be positioned on the patient's tissue.

22. The physiological sensor of claim 21, comprising at least two power generating components, wherein a first power generating component is positioned on a top side of the sensor housing and a second power generating component is positioned on a bottom side of the sensor housing.

23. The monitoring system of claim 16, further comprising a charging control circuitry configured to determine whether a level of charge generated by the power generating component is sufficient to charge an energy storage component of the wireless sensor and to generate an error signal in response to determining that the level of charge is insufficient to charge the energy storage component.

* * * * *